United States Patent [19]

Prescott et al.

[11] 4,209,656
[45] Jun. 24, 1980

[54] SULFURIC ACID CATALYZED ALKYLATION PROCESS

[75] Inventors: Gerald F. Prescott, Bridge City; Charles T. Lewis, Jr., Houston, both of Tex.

[73] Assignee: Texaco Inc., White Plains, N.Y.

[21] Appl. No.: 953,506

[22] Filed: Oct. 23, 1978

[51] Int. Cl.² .............................................. C07C 3/54
[52] U.S. Cl. ................................. 585/715; 585/718; 585/730
[58] Field of Search ................ 260/683.59, 683.62, 260/683.4 F; 585/715

[56] References Cited

U.S. PATENT DOCUMENTS

| | | | |
|---|---|---|---|
| 2,981,771 | 4/1961 | Brant et al. | 260/683.62 |
| 3,043,771 | 7/1962 | Bloch | 260/683.62 |
| 3,162,694 | 12/1964 | Beavon | 260/683.59 |
| 3,168,591 | 2/1965 | Beavon et al. | 260/683.59 |
| 3,256,360 | 6/1966 | Goldsby et al. | 585/715 |
| 3,970,720 | 7/1976 | West | 260/683.62 |

*Primary Examiner*—George Crasanakis
*Attorney, Agent, or Firm*—Carl G. Ries; Robert A. Kulason; James L. Bailey

[57] ABSTRACT

A process for alkylating isoparaffin hydrocarbon with olefin hydrocarbon in the presence of a sulfuric acid alkylation catalyst wherein hydrocarbon effluent from an alkylation reaction zone is treated in the liquid phase with bauxite or similar adsorbent for removing acid alkyl sulfates, neutral alkyl sulfate and other corrosive species, wherein treated alkylation effluent is flashed at reduced pressure in indirect heat exchange contact with alkylation reaction mixture in said alkylation reaction zone for refrigerating said reaction mixture, and wherein flashed vapors and unflashed liquid are fractionated for recovery of isoparaffin recycle and alkylated hydrocarbon product.

3 Claims, 1 Drawing Figure

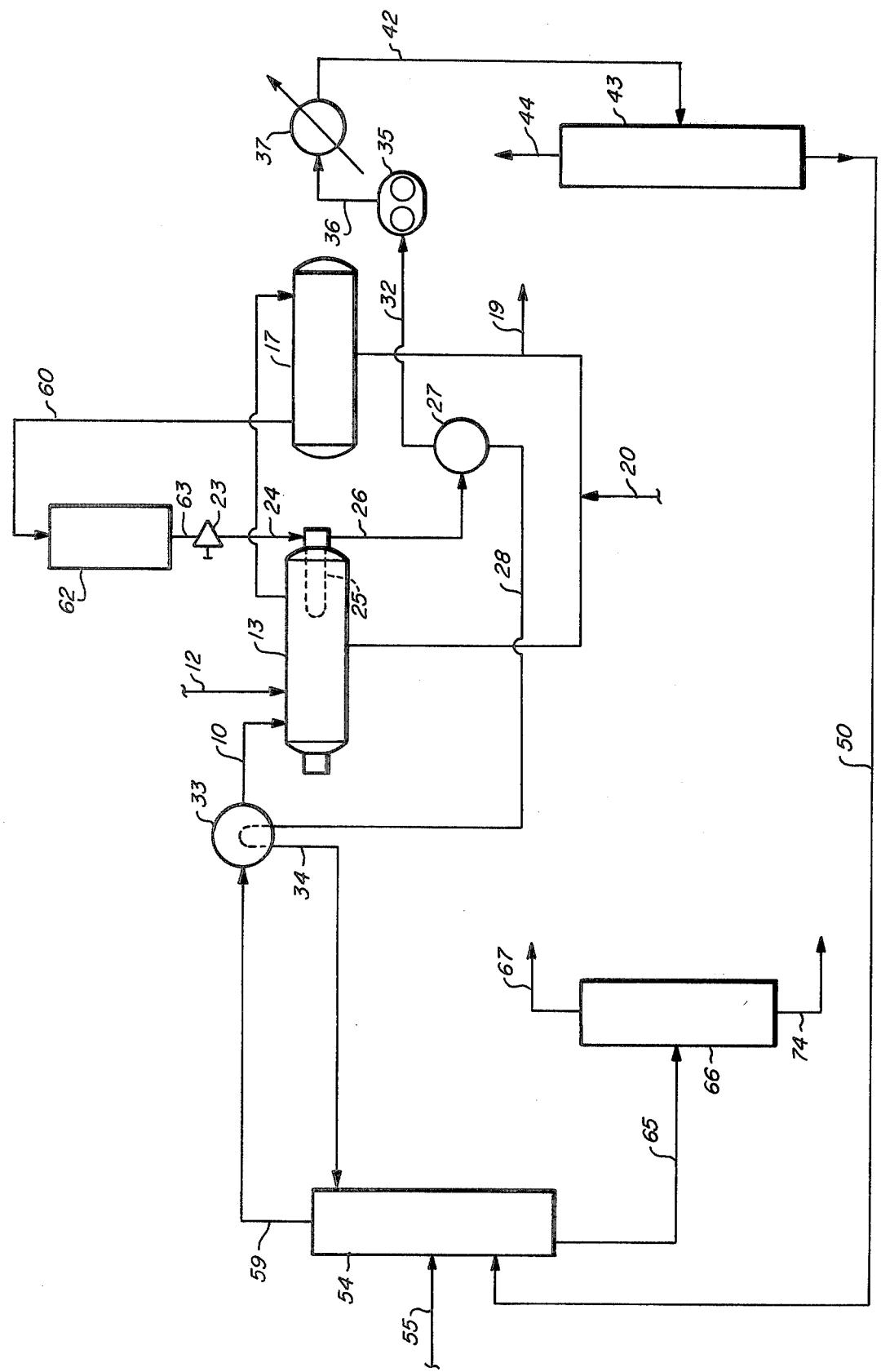

SULFURIC ACID CATALYZED ALKYLATION PROCESS

BACKGROUND OF THE INVENTION

The present invention relates to processes for alkylating isoparaffin hydrocarbons, such as isobutane, with olefin hydrocarbons, such as propylene and/or butylenes, in the presence of a sulfuric acid alkylation catalyst for production of alkylated hydrocarbons, wherein hydrocarbon effluent from an alkylation zone, comprising unreacted isoparaffin hydrocarbon and alkylated hydrocarbons and containing acid alkyl sulfates and dialkyl sulfates and acid oils, is flashed at reduced pressure in indirect heat exchange contact with reaction mixture in said alkylation zone for refrigerating said reaction mixture, and wherein flashed vapor and unflashed liquid from said effluent flashing step is fractionated to recover isoparaffin for recycle and alkylated hydrocarbon product. More particularly, the present invention relates to an improved process wherein hydrocarbon effluent, separated from alkylation catalyst, from the alkylation reaction zone is treated with bauxite or similar adsorbents, for removal of acid alkyl sulfates, dialkyl sulfates and other reactive and corrosive species, prior to flashing said hydrocarbon effluent.

Processes for alkylating low molecular weight isoparaffin hydrocarbons, e.g. isobutane, with low molecular weight olefins, e.g. propylenes and/or butylenes, in the presence of alkylation catalyst comprising sulfuric acid are well known and widely practiced on a commercial scale. Alkylation catalysts for such processes, of interest in the present invention, comprise sulfuric acid. The sulfuric acid may be present in combination with other catalysts, such as fluorosulfonic acid and may be employed with surface active alkylation reaction promoters. In such alkylation reactions, sulfuric acid reacts, in side reactions, with hydrocarbons present to form by product dialkyl sulfates, acid alkyl sulfates, and acid oils. Acid oils are high molecular weight oils containing substantial amounts of sulfur and oxygen. The major portion of such by-products remain in the acid catalyst phase upon separation of an alkylation reaction zone effluent into a hydrocarbon effluent phase and a catalyst phase. However, a substantial portion of such by-products may enter the hydrocarbon effluent phase, particularly dialkyl sulfates and to a lesser extent, acid alkyl sulfates.

In commercial alkylation processes, alkylation reaction hydrocarbon effluent is subjected to fractional distillation for recovery of unreacted isoparaffin and alkylated hydrocarbon product. The unreacted isoparaffin is commonly recycled to the alkylation reaction zone for maintaining the ratio of isoparaffin to olefin reactant above about 2:1. Such fractional distillation is generally accomplished in several fractional distillation columns equipped with reboilers. The by-products, e.g. dialkyl sulfates and acid alkyl sulfates, present in such hydrocarbon effluent are corrosive or breakdown into compounds which are corrosive, under conditions of temperature in such reboilers. Consequently, common practice is to treat hydrocarbon effluent, prior to charge into fractional distillation columns, for removal of corrosive materials.

Hydrocarbon effluent may be treated with caustic materials, such as aqueous caustic solutions, which react with corrosive materials such as acid alkyl sulfates. Alternatively, hydrocarbon effluent may be treated with adsorbents such as bauxite, which adsorb polar compounds which include neutral alkyl sulfates (dialkyl sulfates) as well as acid alkyl sulfates. Bauxite treating of alkylation reaction hydrocarbon effluent has the advantage of removing most polar compounds, and eliminates water carryover with isoparaffin recycle into the alkylation reaction zone, but produces a large amount of spent bauxite for disposal. Caustic treating has the advantage of employing a liquid solution, such that spent liquor may be treated by common techniques and eventually be disposed of. Over the years, caustic treating has substantially replaced bauxite treating for removal of corrosive compounds from alkylation reaction hydrocarbon effluent.

Alkylation reaction processes employing effluent refrigeration are processes wherein an emulsion of acid catalyst and hydrocarbon reactants are contacted with mixing at relatively low temperatures (about $-20°$ to $100°$ F. for processes employing sulfuric acid catalyst) in an alkylation reaction zone; wherein emulsion effluent from said alkylation reaction zone is separated into a hydrocarbon phase and a catalyst phase, wherein the separated hydrocarbon phase is flashed at reduced pressure while in indirect heat exchange contact with emulsion in said alkylation reaction zone for refrigeration of said emulsion, wherein flashed hydrocarbon vapor is fractionated in a first fractionation zone for recovery of isoparaffin for recycle, and wherein unflashed hydrocarbon liquid is fractionated in a second fractionation zone for recovery of isoparaffin for recycle and alkylated hydrocarbon product.

In effluent refrigerated alkylation processes, both the flashed hydrocarbon vapor and unflashed hydrocarbon liquid tend to contain polar compounds, such as dialkyl sulfates and acid alkyl sulfates which are corrosive, or which break-down into corrosive compounds, in the reboilers of the fractionation zones. According to common practice, flashed vapors, after heat exchange, are condensed, scrubbed of reactive compounds in a first aqueous caustic treater, and the caustic scrubbed condensate is fractionated in a first fractionation zone for recovery of isoparaffin for recycle to the alkylation reaction. Unflashed hydrocarbon liquid, after heat exchange, is scrubbed of reactive compounds in a second aqueous caustic treater, and fractionated in a second fractionation zone for recovery of additional isoparaffin for recycle and alkylated hydrocarbon product. Such caustic scrubbing results in water (and sometimes caustic) entering the alkylation process with recycle isobutane. Such water increases acid consumption in the alkylation process. Additionally, caustic scrubbing does not remove dialkyl sulfates, which tend to decompose into acidic materials in the presence of water under conditions of elevated temperature in fractionation zone reboilers.

The two caustic scrubbers could be replaced with two bauxite, or other adsorbent, treaters, thereby eliminating water carry-over problems and removing dialkyl sulfates which decompose into corrosive compounds in fractionator reboilers. This however is not a common practice.

SUMMARY OF THE INVENTION

Now, according to the present invention we have discovered an improved sulfuric acid catalyzed process for alkylating isoparaffin hydrocarbons with olefin hydrocarbons, employing flashed effluent refrigeration of the alkylation reaction emulsion, wherein the improvement comprises treating a separated hydrocarbon phase from an alkylation reaction zone with bauxite, or similar adsorbent, prior to flashing said hydrocarbon phase.

In one embodiment of the present invention, wherein isobutane is contacted with olefin selected from propylene and/or butylene at an isobutane/olefin molar ratio in the range of about 2:1 to 20:1, in an alkylation reaction zone, in the presence of sulfuric acid alkylation catalyst, at a temperature in the range of about $-20°$ to about $100°$ F., at a pressure sufficient to maintain reactants in the liquid phase, under conditions of agitation sufficient to maintain a hydrocarbon-catalyst emulsion, wherein alkylation reaction emulsion is separated, in a settling zone, into a catalyst phase and a hydrocarbon phase substantially free of catalyst, wherein a major portion of said separated catalyst phase is recycled to said alkylation reaction zone, wherein said separated hydrocarbon phase is flashed at reduced pressure, in a flash zone, for forming cold flashed vapor and cold unflashed liquid, wherein said cold vapor and cold liquid hydrocarbons in said flash zone are brought into indirect heat exchange contact with said reaction emulsion in said alkylation reaction zone for refrigerating said alkylation reaction emulsion, wherein flashed vapor from said flash zone is compressed and condensed into a condensed hydrocarbon phase for charge into a first fractionation zone, and wherein said unflashed hydrocarbon liquid is charged into a second fractionation zone, the improvement which comprises:

(a) treating said separated hydrocarbon phase, at a temperature in the range of about $-20°$ to about $100°$ F., and a pressure in the range of about atmospheric to about 400 psig with bauxite prior to flashing said separated hydrocarbon phase, for removing polar compounds from said separated hydrocarbon phase.

The advantages of the improvement of the present invention over processes of the prior art include: removing substantially all polar compounds from the separated hydrocarbon phase prior to the flashing step, thereby reducing corrosion in the flash zone and the succeeding fractionation zones. Additionally, only one bauxite treater is required, as replacement for two caustic treaters commonly used in prior art processes.

These and other advantages will be discussed in the detailed description which follows.

BRIEF DESCRIPTION OF THE DRAWING

The drawing is a schematic representation of an alkylation process employing the improvement of the present invention.

DETAILED DESCRIPTION

Broadly, the catalytic alkylation process contemplated herein comprises reacting isobutane in molar excess with an olefin based alkylatable material, e.g. butylene and propylene, in the liquid phase in an alkylation zone in the presence of an alkylation catalyst comprising sulfuric acid. The alkylation zone is refrigerated by flash vaporization of volatile hydrocarbons, including isobutane and inert propane, at reduced pressure, from the resulting alkylation zone hydrocarbon effluent, thereby forming a hydrocarbon vapor phase containing isobutane and lighter hydrocarbons and an unvaporized hydrocarbon liquid phase containing isobutane, alkylate hydrocarbons and butane diluent. Isobutane is recovered from the hydrocarbon vapor phase by fractionation in a first fractionation zone, and from the unvaporized hydrocarbon liquid phase by fractionation in a second fractionation zone. The improvement of the present invention comprises treating alkylation zone hydrocarbon effluent with bauxite, or other solid adsorbent, for removal of polar compounds including dialkyl sulfates, acid alkyl sulfates, etc. prior to flash vaporization. Such bauxite treating eliminates the necessity of separately treating the hydrocarbon vapor phase and the unvaporized hydrocarbon phase prior to fractionation, and by removing corrosive materials, reduces corrosion of equipment employed in the flash vaporization and refrigeration steps.

Catalysts contemplated for use in the process of the present invention are those comprising sulfuric acid. That is, sulfuric acid of about 90 to 98% concentration, mixtures of sulfuric acid with other alkylation catalysts such as fluorosulfonic acid, and such catalysts containing surface active compounds and/or alkylation reaction promoters. Such sulfuric acid containing catalysts react with hydrocarbons in the alkylation zone to produce reaction by-products such as acid alkyl sulfates and dialkyl sulfates, which are corrosive or which break down into corrosive materials in process equipment such as fractionator reboilers. Although such by-product compounds are generally soluble in the alkylation catalyst phase, a significant portion are present in the alkylation reaction hydrocarbon effluent, such that corrosion is a serious problem requiring treatment to protect alkylation and fractionation process equipment.

Generally, isobutane is the preferred isoparaffin charge for the alkylation process. The olefin based alkylatable material is preferably propylene and/or butylenes. Propylene is commonly promoted with 5–20 percent butylene. Such olefin charge streams generally contain diluent hydrocarbons such as propane and butane.

In order to more completely describe the improvement of the present invention, attention is now brought to the drawing. The drawing is a schematic representation of an alkylation process embodying the improvement of the present invention. For clarity, only those elements necessary for a complete description of the present invention are included in the drawing, and elements such as pumps, valves, instrumentation, etc. commonly employed in such processes, but not necessary to describe the invention, have been omitted.

The drawing, and following descriptions are by way of example only, and are not intended to limit the scope of the present invention which is set-out in the appended claims.

In the drawing, an alkylation process for producing 3000 B/D (barrels per day) alkylate hydrocarbon is described. An isobutane stream in the amount of 28,000 B/D, comprising 92% isobutane, 4% n-butane and 4% propane flows through vapor line 59, from deisobutanizer 54, into heat exchanger 33, and is fed through line 10 into alkylation reaction zone 13.

An olefin feed stream comprising 507 B/D propylene, 1180 B/D butylenes, 500 B/D isobutane, and 650 B/D propane and butane diluents is fed through line 12 into alkylation reaction zone 13. Temperature in the alkylation reaction zone is maintained at 45° F. and the pressure at 50 psig, whereby reactants are maintained in the liquid phase. Alkylation reaction effluent, comprising an emulsion of a hydrocarbon effluent phase and a catalyst phase as hereinbelow described, flows from alkylation reaction zone 13 via line 14 into acid settler 17. In acid settling zone 17, alkylation reaction effluent separates under influence of gravity, into an alkylation reaction hydrocarbon effluent phase and a catalyst phase. The catalyst phase is recycled via line 18 to the alkylation reaction zone 13 for contact with reactant hydrocarbons, as hereinabove described. The volume ratio of hydrocarbon phase to catalyst phase in alkylation reaction zone 13 is maintained at about 1:1. Alkylation catalyst is maintained at about 92% sulfuric acid concentration by purging a minor portion of catalyst from line 18 via line 19 and adding make-up sulfuric acid of 99% concentration via line 20.

A major portion of acid alkyl sulfates, dialkyl sulfates, acid oils, water, and other corrosive and polar compounds remain with the separated acid catalyst phase. A minor portion of such compounds are present in the alkylation reaction hydrocarbon effluent phase. Such polar compounds, particularly acid alkyl sulfates and dialkyl sulfates in the presence of water are corrosive, and if allowed will cause severe corrosion and plugging in alkylation process equipment.

In the drawing, according to the improvement of the present invention, alkylation reaction hydrocarbon effluent separated from catalyst phase in acid settling zone 17, flows via line 60 for contact with bauxite adsorbent in bauxite treating zone 62. In treating zone 62, alkylation reaction hydrocarbon effluent phase is flowed through a first bed of bauxite at a temperature in the range of about $-20°$ to about $100°$ F., at a superatmospheric pressure sufficient to maintain isobutane in the liquid phase, at a liquid hourly space velocity in the range of about 0.1 to about 10 vol. hydrocarbon/hr/vol. bauxite, whereupon polar compounds are essentially completely removed from said hydrocarbon effluent phase. That is, acid alkyl sulfates, dialkyl sulfates, and other polar compounds are removed from the hydrocarbon effluent phase and are absorbed upon the bauxite. Flow of hydrocarbon effluent through bauxite in treating zone 62 is continued until the bauxite becomes spent and such polar compounds begin passing unabsorbed through treating zone 62. Upon such breakthrough of polar compounds, hydrocarbon effluent phase is routed to a second bed of bauxite, not shown, and spent bauxite in said first bed is regenerated or replaced with fresh bauxite.

In the drawing, from bauxite treating zone 62, treated hydrocarbon effluent flows through line 62 to pressure reduction valve 23. In pressure reduction valve 23, treated hydrocarbon effluent, which comprises about 80% isobutane and which contains propane and butane diluents, is flash vaporized under adiabatic conditions by reducing the pressure to about 5 psig such that a chilled vapor-liquid mixture is formed.

In the drawing, chilled vapor-liquid mixture from valve 23 flows via line 24 into cooling coil 25 suspended within alkylation reaction zone 13. In cooling coil 25, the chilled vapor-liquid mixture refrigerates, by indirect heat exchange, alkylation reaction mixture in alkylation reaction zone 13, to maintain the desired $45°$ F. reaction temperature.

In the drawing, from cooling coil 25, the vapor-liquid mixture flows via line 26 into vapor-liquid separation zone 27 wherein separated vapors, (equivalent to 8,000 B/D liquid) are removed via line 32, and wherein separated liquids (amounting to 22,2000 B/D) are withdrawn via line 28.

In the drawing, separated liquid flows via line 28 to heat exchanger 33 wherein, by indirect heat exchange, it is employed to cool the isobutane stream, as hereinbefore described. From heat exchanger 33, separated liquid flows via line 34 to deisobutanizer fractionation zone 54 for recovery of isobutane, as will hereinafter be described.

In the drawing, separated vapors from vapor-liquid separator 27 pass through line 32, and are compressed in compressor 35 to a pressure of about 130 psia. From compressor 35, the compressed vapors flow via line 36 to condenser 37, wherein they are condensed by indirect heat exchange with cooling water. From condenser 37, condensed hydrocarbon flows via line 42 to depropanizer fractionation zone 43. In depropanizer fractionation zone 43, condensed hydrocarbon is fractionated into a propane fraction (about 500 B/D) and an isobutane fraction containing less than 5% propane. Propane fraction is withdrawn from the process via line 44.

In the drawing, depropanizer isobutane fraction flows from depropanizer zone 43 via line 50 as charge to deisobutanizer fractionation zone 54.

In the drawing, isobutane make-up for the alkylation process comprising about 1550 B/D isobutane and 1350 B/D n-butane is charged to deisobutanizer fractionation zone 54 via line 55.

In the drawing, in deisobutanizer fractionation zone 54, isobutane make-up from line 55, depropanizer isobutane fraction from line 50, and separated liquid hydrocarbon from line 34 are fractionated to yield an overhead fraction comprising isobutane, and a bottoms fraction comprising n-butane and alkylate hydrocarbon. The deisobutanizer zone overhead isobutane fraction flows via line 59 to the alkylation process, as hereinbefore described. Deisobutanizer bottoms fraction flows from deisobutanizer fractionation zone 54 via line 65 to debutanizer fractionation zone 66. In debutanizer fractionation zone 66, deisobutanizer bottoms fraction is fractionated into a n-butane overhead fraction and a $C_5^+$ alkylate bottom fraction. The n-butane overhead fraction is withdrawn from the process via line 67. The $C_5^+$ alkylate fraction is withdrawn from debutanizer fractionation zone 66 via line 74 for motor fuel blending. This alkylate fraction is substantially free of water, sulfur compounds and other polar compounds which may affect motor fuel quality.

Thus, according to the preceeding drawing and description, sulfuric acid catalyzed processes for alkylating isobutane with olefins are disclosed which employ effluent refrigeration in the alkylation reaction zone, and which employ bauxite treatment of alkylation reaction effluent hydrocarbon for removal of corrosive polar compounds prior to contact of said effluent with equipment within the alkylation process.

Modifications and variations of the process disclosed herein will be obvious to those skilled in the art, which modifications and variations are within the spirit and scope of the invention. Therefore, the only limitations intended for the present invention are those encompassed within the appended claims.

We claim:

1. In an effluent refrigerated alkylation process for alkylating isobutane with propylene and/or butylenes in the presence of an alkylation catalyst comprising sulfuric acid wherein polar compounds including acid alkyl sulfates, and dialkyl sulfates are present in corrosive amounts in an alkylation reaction zone hydrocarbon effluent, the improvement which comprises:

(a) reacting, in an alkylation zone, a molar excess of isobutane with olefin hydrocarbon selected from butylenes and mixtures of butylenes and propylene, in the presence of an alkylation catalyst comprising sulfuric acid, at alkylation conditions including a temperature in the range of about $-20°$ to $100°$ F., and a superatmospheric pressure sufficient to maintain reactants in the liquid phase for producing an alkylation reaction zone effluent emulsion comprising alkylation catalyst, alkylated hydrocarbons, and unreacted isobutane;

(b) separating, in a catalyst separation zone, said alkylation reaction effluent into an acid catalyst phase and an alkylation reaction hydrocarbon effluent phase comprising alkylated hydrocarbon and unreacted isobutane, and containing corrosive amounts of polar compounds including acid alkyl sulfates and dialkylsulfates;

(c) contacting, in a treating zone, said alkylation reaction hydrocarbon effluent, in the liquid phase, with solid adsorbent for adsorbing said polar compounds and producing a treated hydrocarbon effluent substantially free of corrosive polar compounds;

(d) flashing, by adiabatic expansion at a reduced pressure, said treated hydrocarbon effluent for producing a chilled mixture of hydrocarbon vapor and hydrocarbon liquid;

(e) exchanging heat, in an indirect heat exchange zone, from said alkylation reaction zone emulsion to said chilled hydrocarbon vapor-liquid mixture for maintaining a selected alkylation reaction temperature; and (f) separating, in a vapor-liquid separation zone, said hydrocarbon vapor-liquid mixture into a hydrocarbon vapor phase comprising isobutane and a hydrocarbon liquid phase comprising isobutane and alkylated hydrocarbon;

(g) fractionating said hydrocarbon vapor phase for recovery of isobutane for recycle to said alkylation reaction zone;

(h) fractionating, said hydrocarbon liquid phase for recovery of an alkylated hydrocarbon product fraction and isobutane for recycle to said alkylation reaction zone.

2. The method of claim 1 wherein said solid adsorbent is bauxite.

3. The method of claim 2 wherein said alkylation reaction effluent is contacted, in said treating zone, with said bauxite at a temperature in the range of about $-20°$ to about $100°$ F., at a superatmospheric pressure sufficient to maintain said hydrocarbon effluent in the liquid phase, and at a liquid hour space velocity in the range of about 0.1 to about 10 volumes hydrocarbon/hr/volume bauxite for adsorbing substantially all dialkyl sulfates and acid alkyl sulfates from said hydrocarbon effluent.